United States Patent [19]

Kavteladze et al.

[11] Patent Number: 5,707,376
[45] Date of Patent: Jan. 13, 1998

[54] STENT INTRODUCER AND METHOD OF USE

[75] Inventors: Zaza A. Kavteladze; Aleksandr P. Korshok, both of Moscow, Russian Federation; Scott E. Boatman, Bloomington, Ind.

[73] Assignees: William Cook Europe A/S, Bjaeverskov, Denmark; Cook Incorporated, Bloomington, Ind.

[21] Appl. No.: 475,117

[22] Filed: Jun. 7, 1995

Related U.S. Application Data

[63] Continuation-in-part of Ser. No. 450,009, May 25, 1995, which is a continuation-in-part of Ser. No. 34,346, Feb. 2, 1995, which is a continuation-in-part of Ser. No. 379,582, filed as PCT/DK93/00256, Aug. 6, 1993.

[51] Int. Cl.⁶ .................................................. A61B 17/00
[52] U.S. Cl. ............................................................ 606/108
[58] Field of Search .................................. 606/108, 109

[56] References Cited

U.S. PATENT DOCUMENTS

| | | |
|---|---|---|
| 4,503,569 | 3/1985 | Dotter . |
| 4,665,918 | 5/1987 | Garza et al. ............... 606/108 |
| 5,037,427 | 8/1991 | Harada et al. . |
| 5,102,417 | 4/1992 | Palmaz . |
| 5,135,536 | 8/1992 | Hillstead . |
| 5,234,457 | 8/1993 | Andersen . |
| 5,290,310 | 3/1994 | Makower et al. ........... 606/108 X |
| 5,306,294 | 4/1994 | Winston et al. ............... 623/1 |
| 5,346,498 | 9/1994 | Greelis et al. ............... 606/108 |
| 5,354,308 | 10/1994 | Simon et al. . |
| 5,360,443 | 11/1994 | Barone et al. . |
| 5,366,472 | 11/1994 | Hillstead . |
| 5,397,359 | 3/1995 | Mittelmeier et al. . |
| 5,405,377 | 4/1995 | Cragg . |

FOREIGN PATENT DOCUMENTS

| | | |
|---|---|---|
| 0221570 | 5/1987 | European Pat. Off. . |
| 0464755 | 1/1992 | European Pat. Off. . |
| 3918736 | 12/1990 | Germany . |
| 1237201 | 3/1981 | U.S.S.R. . |

OTHER PUBLICATIONS

Rosch, J., et al., "Modified Gianturco Expandable Wire Stents in Experimental and Clinical Use," *Ann. Radiol.*, 1988, vol. 31, No. 2, pp. 100–103.

*Primary Examiner*—Michael H. Thaler
*Attorney, Agent, or Firm*—Richard J. Godlewski

[57] ABSTRACT

An introducer (10) method of percutaneously deploying a self-expanding stent (14) in a body vessel or duct (43). The stent introducer includes an outer elongated member tube (11) having a passage (12) extending longitudinally therein and operable in a first direction (13) for deploying the self-expanding stent in a collapsed condition from the outer member passage. An inner elongated member (15) is positioned in the outer member passage and is operable in a second direction (16) for deploying the stent from the outer member passage. An interconnection mechanism (17) is connected to the outer and inner members for operation thereof, whereby a stent in a collapsed condition is deployed from the outer member passage to an expanded condition. When deployed, the expanded portion of the stent remains fixedly positioned longitudinally in the body vessel or duct as the remaining portion is deployed from the outer member passage. The inner member operates a second operable distance (34) and includes at least one protuberance (19) for pushing the stent out of the outer member passage as the outer member is concomitantly withdrawn a first operable distance (33) from the collapsed, self-expanding stent. The first operable distance is the short length (36) of the stent in an expanded condition, whereas the second operable distance (34) is approximately the distance (37) in the long and short lengths of the stent. The interconnection mechanism of the introducer further includes a transfer assembly (23) coupled to the outer and inner members for controlling the travel distance and direction thereof.

20 Claims, 5 Drawing Sheets

STENT INTRODUCER AND METHOD OF USE

CROSS-REFERENCE TO RELATED APPLICATIONS

This application is a continuation-in-part of copending U.S. utility patent application Ser. No. 08/450,009, filed May 25, 1995, entitled "An Implantable, Self-Expanding Prosthetic Device", which application is a continuation-in-part of copending U.S. Design patent application Ser. No. 29/034,346, filed Feb. 2, 1995, entitled "An Implantable, Self-Expanding Stent" and commonly assigned herewith, which application is a continuation-in-part of U.S. Utility patent application Ser. No. 08/379,582, filed Feb. 1, 1995, entitled "A Prosthetic Device for Sustaining a Blood Vessel or Hollow Organ Lumen," which application is the U.S. national phase of International Patent Application No. PCT/DK93/00256, filed Aug. 6, 1993, which application claims priority to Russian Application No. 5057852, filed Aug. 6, 1992 (now Reg. No. 35-13-426, granted Feb. 18, 1993).

TECHNICAL FIELD

This invention relates generally to implantable medical devices and, in particular, to an introducer and a method of using the introducer for percutaneously implanting a self-expanding stent to sustain a body vessel or duct.

BACKGROUND OF THE INVENTION

Various diseases of blood vessels or hollow organs cause a stenosis or complete obturation (occlusion) of their lumen, which results in a decrease or complete loss of their functional attributes. The wide spread of diseases of this kind demands an elaboration of new methods of medical treatment. Prosthetic devices for sustaining a blood vessel or hollow organ lumen typically have a tubular shaped frame body which is introduced in the vessel or hollow organ and fixed in the necessary place to sustain its lumen.

One such prosthetic device includes a tubular shaped wire frame with a plurality of interconnected cells and flexible interconnections. The device is collapsed for introduction into the body of a patient by pulling on the opposite ends thereof. The collapsed device is contained in a tubular sheath. When the device is positioned in the occluded region of a body passage or vessel, it is released from the tubular sheath and permitted to expand radially against the wall of the body passage. A problem with the use of this device is that the device shortens longitudinally from both ends of the device toward the longitudinal center thereof during expansion. The physician cannot control the longitudinal shortening of the device once released from the tubular sheath. As a result, the device potentially shifts longitudinally along the body passage and away from the occlusion into a portion of the passage with a larger cross-sectional area. The problem is compounded with the use of prosthetic devices in which the tubular wire frame includes interconnected cells that spiral around the circumference of the device. In these prosthetic devices, the radial collapse and expansion of the device is performed by twisting the opposite ends respectively toward and away from each other.

SUMMARY OF THE INVENTION

The foregoing problems are solved and a technical advance is achieved in an illustrative stent introducer having coaxial inner and outer elongated members for concomitant deployment of a collapsed stent from a passage of the outer member. The outer member of the introducer is operated and preferably pulled back in a first direction from the collapsed stent contained therein, whereas the inner member is concomitantly operated and preferably pushed forward for pushing the collapsed stent out of the outer member passage. Advantageously, this concomitant deployment expands the collapsed stent in the vessel of a patient without longitudinally moving the stent from the designated deployment site.

The stent introducer also includes an interconnection mechanism for pulling the outer member back and concomitantly pushing the inner member forward. The interconnection member is advantageously manually operated by the physician with either left- or right-hand operation. The interconnection mechanism includes a first carrier connected to the outer member for operating the outer member and a second carrier connected to the inner member for operating the inner member. A transfer assembly is coupled to an input member and at least one of the first and second carriers. To operate the inner and outer members in opposite directions, the transfer assembly advantageously includes a drive member gear coupled to the input member with an intermediate member gear coupled to one of the first and second carriers. The drive and intermediate member gears are selected to operate the inner and outer members predetermined first and second distances for advantageously deploying the stent without longitudinal movement of the stent in the body vessel or duct as the expanding stent is being deployed from the outer member passage.

The first carrier of the interconnection mechanism includes a passage extending longitudinally therethrough for extending the inner member through the carrier passage and for operating the inner member in a direction opposite to that of the outer member. The first carrier also includes a sideport which communicates with the carrier passage as well as the outer member passage for advantageously administering contrast medium and medications to the patient.

The interconnection mechanism further includes a lock that is engageable with at least one of the first and second carriers for limiting movement thereof and preventing premature deployment of the stent during the placement procedure.

As previously suggested, the outer member is operated in a first direction for a first distance which is at least the short length of the stent in an expanded condition. The operable distance of the inner member is traversed in a second direction opposite to that of the outer member and is approximately the difference in the long and short lengths of the stent. The long length of the stent is the length of the stent in a collapsed condition within the passage of the outer member. These first and second operable distances are selected so that the distal end of a stent being deployed from the outer member passage remains fixedly positioned longitudinally relative to the interconnection mechanism as well as the occlusion site.

To maintain the longitudinal positioning of the deployed stent, the inner member of the introducer includes at least one protuberance for pushing the stent out of the outer member passage as the outer member is withdrawn from the collapsed stent. Alternatively, the introducer can advantageously include a protuberance positioned about the distal end of the inner member for pulling and, more particularly, ratcheting the stent out of the outer member passage with back-and-forth longitudinal movements. To assist in the placement of the collapsed stent in the body vessel or duct, the inner member also includes first and second radiopaque markers positioned about the distal end of the inner member and on either side of the occlusion site for indicating placement of the expanded stent.

The method of percutaneously deploying a self-expanding stent in a body vessel or duct includes positioning the self-expanding stent in a collapsed condition around the inner member and in the outer member passage of the introducer. The stent introducer and collapsed stent are percutaneously introduced to a designated position in a body vessel or duct. The radiopaque markers on the inner member are positioned on either side of the occlusion site to indicate positioning of the stent when fully expanded. When so positioned, the distal portion of the self-expanding stent is deployed from the outer member passage with the assistance of the inner member to an expanded condition at the designated occlusion site. The remaining portion of the stent is then deployed from the outer member passage, again with the assistance of the inner member, with the distal portion of the self-expanding stent remaining fixedly positioned longitudinally as the remaining portion is deployed from the outer member passage. Deployment of the distal portion includes withdrawing the outer member from the stent and pushing the outer member out of the outer member passage to advantageously control the release and deployment of the stent from its collapsed condition to its fully deployed and expanded condition at the occlusion site.

DETAILED DESCRIPTION

Figure 1:
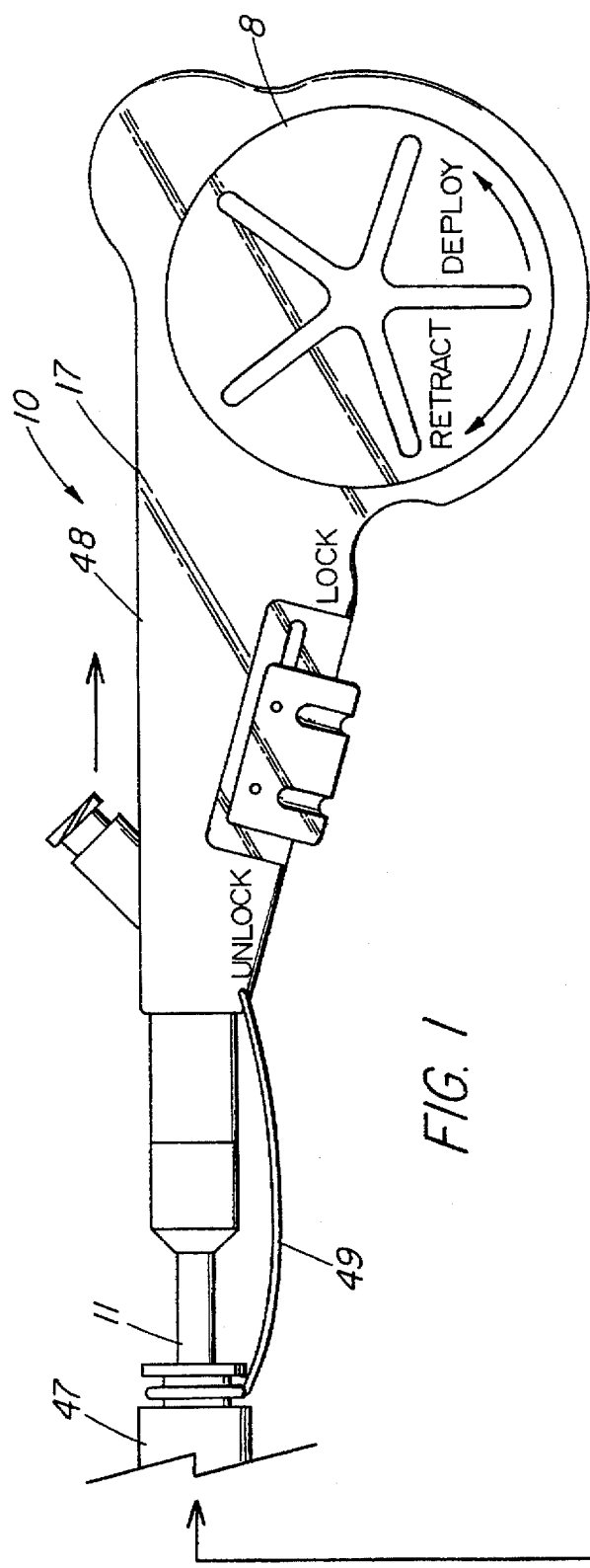
FIG. 1 depicts an illustrative embodiment of the stent introducer of the present invention.
Figure 1:
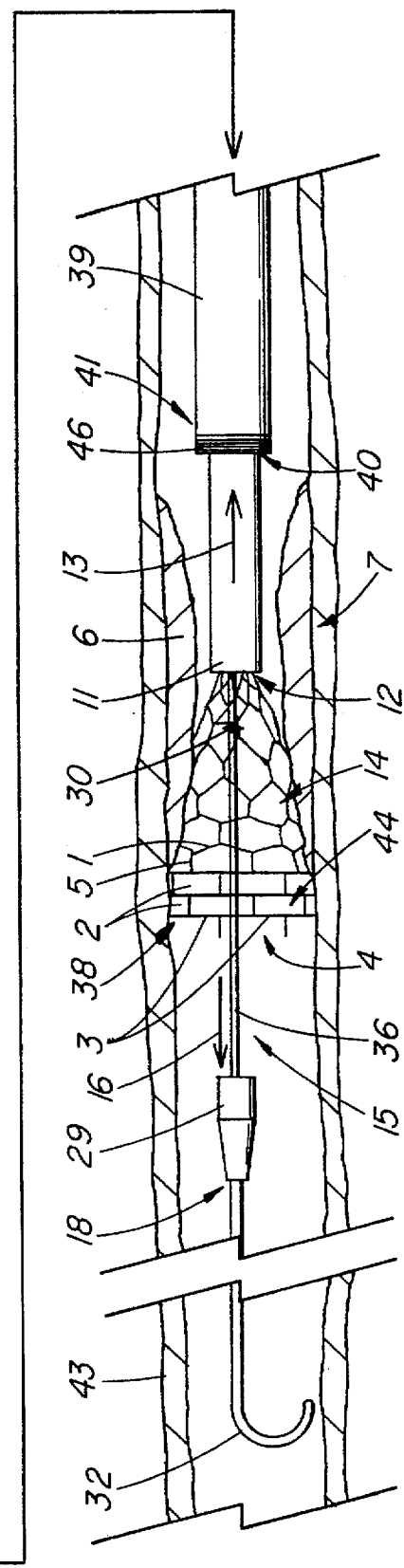

FIG. 1 depicts an illustrative embodiment of stent introducer 10 for percutaneously deploying self-expanding stent 14 in body vessel or duct 43. Self-expanding stent 14 is used in the treatment of various occlusive conditions such as arteriosclerotic iliac artery stenosis and provides mechanical support to compress intimal flaps and dissections against the vessel wall after percutaneous transluminal angioplasty. Additionally, the self-expanding stent mechanically supports arterial sclerotic plaque 6 in the vessel passage, which inhibits restenosis and occlusion. Stent 14 is described in detail in the aforementioned related applications, which are incorporated herein by reference. Briefly, self-expanding stent 14 comprises a wire frame 1 having a flexible tubular shape with rows of interconnected cells 2, each cell having a long axis and a short axis. The cells are arranged with the long axis in the circumferential direction of the frame and with the short axis parallel to the longitudinal axis of the frame. Each cell is formed by two U-shaped wire sections 3. In a plane perpendicular to the longitudinal axis of the frame, one of the branches of the U-shaped wire sections in one row form together a closed ring shape 4, which provides the frame with large radial stiffness for maintaining the vessel passage. In the axial or longitudinal direction, the frame has only low stiffness so that it easily conforms to the vessel wall. Furthermore, the low stiffness in the axial direction allows the stent to be longitudinally elongated for loading into outer elongated member 11 of introducer 10. Interconnections 5 between the U-shaped cells are flexible to further ease loading and deployment of the self-expanding stent into the introducer. The frame of the stent is preferably formed from a wire of superelastic material such as a nickel-titanium alloy to enhance the self-expanding aspect of the stent.

As depicted, stent introducer 10 includes outer elongated member 11 such as, for example, a polytetrafluoroethylene tube, which is percutaneously introduced into body vessel or duct 43 with the aid of introducer sheath 39. The introducer sheath includes a radiopaque marker 46 at its distal end 41 for radiographic visualization thereof. Outer member tube 11 of introducer 10 is inserted through longitudinal passage 40 of introducer sheath 39. After positioning introducer 10 at occlusion site 7 in body vessel or duct 43, collapsed, self-expanding stent 14 is deployed from introducer 10 by operating and, in particular, moving outer member 11 in operable direction 13 and inner member 15 in operable direction 16. Inner elongated member 15 is coaxially positioned in outer member tube 11 and has at least one protuberance proximal of distal end 18 for deploying the stent and, in particular, engaging the collapsed condition stent and pushing it out of outer member passage 12.

Interconnection mechanism 17 of introducer 10 is connected to the outer and inner members and is operable for concomitantly operating the outer member in operable direction 13 and the inner member in operable direction 16. As a result, distal end 38 and distal portion 44 of the stent remain fixedly or stationarily deployed longitudinally in body vessel or duct 43. Furthermore, as the stent is deployed from outer member 11, the cells of the stent fully expand to provide maximum support against radial compression of the vessel or, more particularly, occlusion of the body vessel or duct.

The interconnections of the stent cells have been formed to minimize spiral or rotational motion of the stent as it is deployed from the introducer. As a result, the stent assumes a collapsed condition by pulling longitudinally on the ends of the stent and stretching it. When stretched, the stent is sized for loading in outer member 11. However, when deployed from the introducer, expansion of the stent must be controlled so as to maintain proper longitudinal positioning at the occlusion site.

To further aid in the placement of the self-expanding stent, inner member 15 also includes radiopaque markers 29 and 30, which are spaced apart and positioned about distal end 18 of the inner member. Radiopaque markers 29 and 30 are spaced apart the short longitudinal length 36 (of FIG. 3) of stent 14 in a fully expanded condition. As a result, these radiopaque markers on inner member 15 can be used to accurately position stent 14 in a fully expanded condition with respect to occlusion site 7 in the body vessel or duct. By way of example, stent 14 in a fully expanded condition would have a 10 mm diameter and a short longitudinal length of approximately 40 mm. As a result, the spacing between radiopaque markers 29 and 30 would also be approximately 40 mm and approximate the length of the stent in the fully expanded condition. The radiopaque markers on inner member 15 would thus be initially positioned in body vessel or duct 43 at designated position 42 (FIGS. 2 and 3) straddling occlusion site 7. This placement would indicate the position of the fully expanded stent in body vessel or duct 43.

By way of further example, stent 14 in a collapsed position is positioned in outer member passage 12 and has a long length of approximately 155 mm. To fixedly or stationarily position stent 14 in body passage 43 as it is deployed from introducer 10, outer member 11 is operated and, in particular, pulled back a first operable distance 33 (FIG. 2), which is at least equivalent to the short length of the stent in an expanded condition. Concomitantly, inner member 15 is operated and, in particular, pushed forward a second operable distance 34 (FIG. 3), which approximates the difference in the long and short lengths of the stent. Further to the example, with the long length of the stent in a collapsed condition being approximately 155 mm and the short length of the stent in a fully expanded condition being approximately 40 mm, interconnection mechanism 17 would push forward inner member 15 approximately 115 mm while concomitantly pulling back or withdrawing outer member 40 mm. This concomitant movement of the inner and outer members deploys the collapsed stent to a fully expanded condition at desired longitudinal position 42 in the body vessel, which was initially indicated by radiopaque markers 29 and 30. To maintain fixed or stationary longitudinal placement of the self-expanding stent, the spacing between handle casing 48 of interconnection member 17 and connector hub 47 of introducer sheath 39 is kept constant by the attending physician. This can also be accomplished with spacer bracket 49 that bridges the distal end of casing handle 47 and connector hub 47.

Since inner member 15 is extended distally beyond the occlusion site during deployment of the stent, distal end 18 of the inner member includes an atraumatic filiform curved wire guide 32. This filiform curved wire guide is well-known and attached in a well-known and convenient manner to distal end 18 of the inner member. This atraumatic wire guide prevents trauma to the body vessel as the inner member is extended distally beyond the occlusion site.

Figure 2:
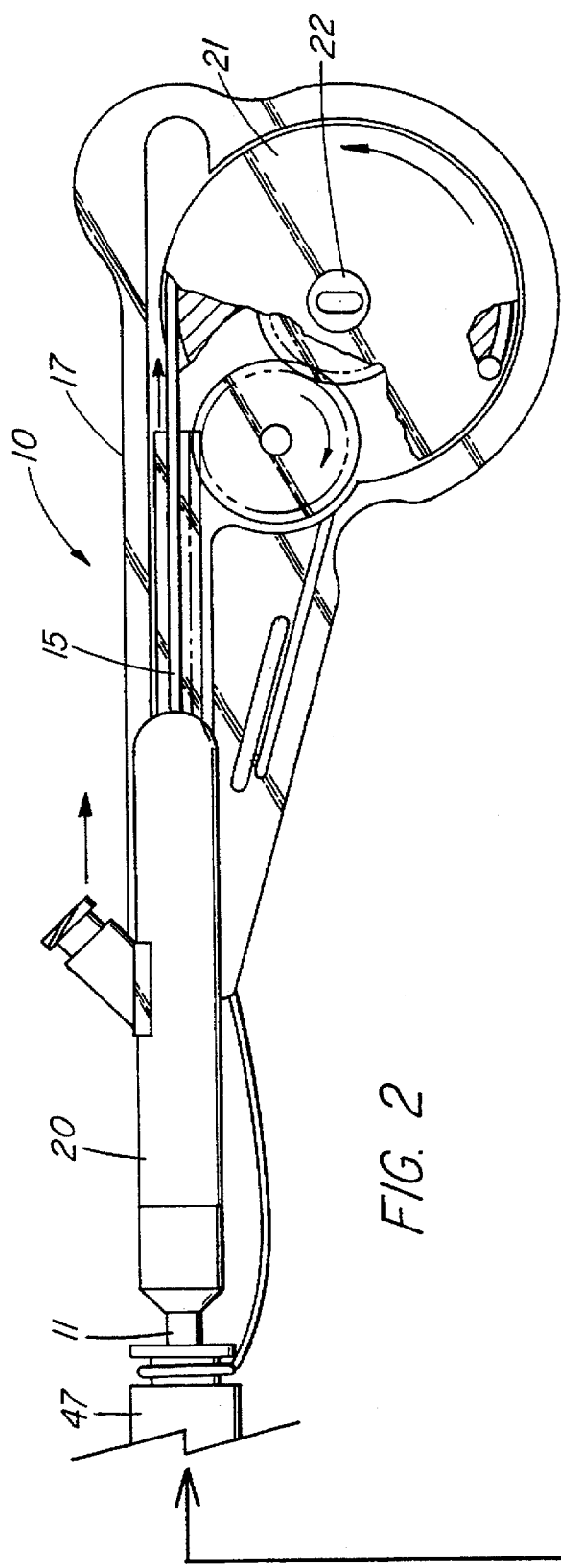
FIG. 2 depicts a partially sectioned view of the introducer of FIG. 1 with a self-expanding stent contained therein and in a collapsed condition.
Figure 2:
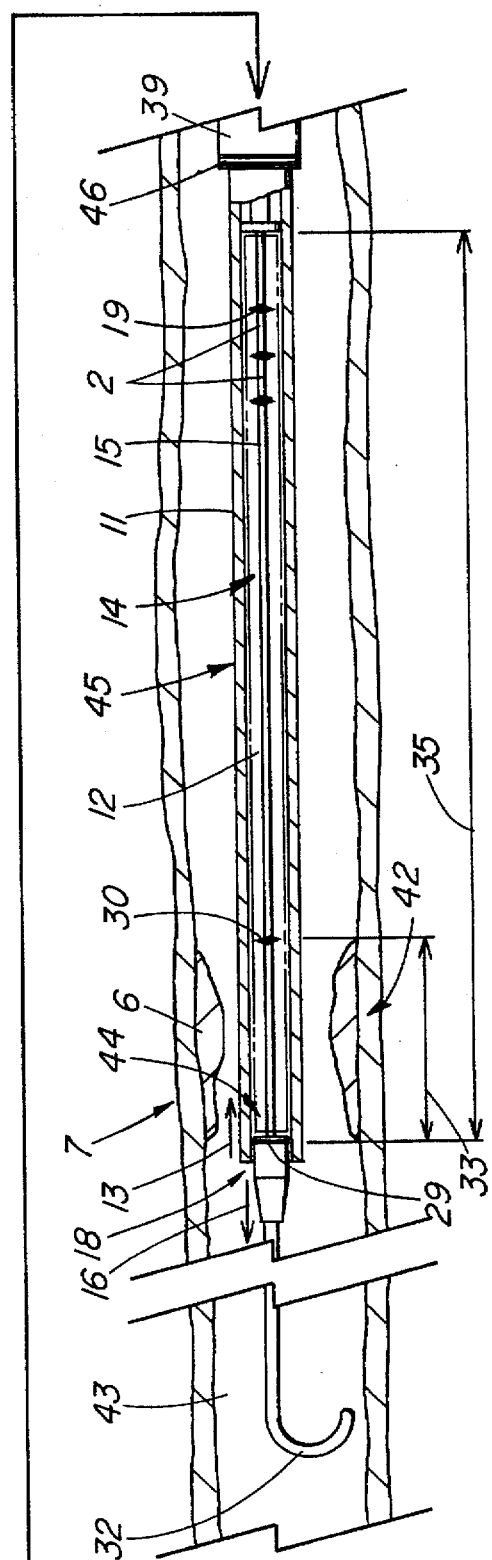

FIG. 2 depicts a partially sectioned view of the introducer 10 of FIG. 1 with self-expanding stent 14 contained therein and in a collapsed condition. Self-expanding stent 14 is positioned in a collapsed condition around inner member 15 and in passage 12 of outer member 11 of the stent introducer. The method of percutaneously deploying the self-expanding stent in body vessel or duct 43 further includes percutaneously introducing the self-expanding stent positioned in the stent introducer to a designated position 42 such as at occlusion site 7 and body vessel 43. Introducer 10 and stent 14 are percutaneously introduced through introducer sheath 39 using the well-known Seldinger technique for percutaneous vascular entry. Prior to introducing stent introducer 10 and self-expanding stent 14 into the vascular system, an angioplasty balloon catheter is introduced through sheath 39, and a well-known balloon angioplasty procedure is performed at occlusion site 7. Radiographic visualization of the procedure is performed with radiopaque marker 46 at the distal end of the introducer sheath along with well-known markers positioned on the balloon angioplasty catheter. The balloon catheter is then removed and the introducer sheath advanced through the occlusion site. The collapsed stent, which is positioned in outer member tube 11 of the introducer, is then passed through the introducer sheath beyond the occlusion site. The introducer sheath is then pulled back through the occlusion site leaving the distal end of outer member 11 positioned through the occlusion site. Radiographic visualization and predeployed positioning of the stent is performed by straddling radiopaque markers 29 and 30 on either side of occlusion site 7.

As previously suggested, a plurality of protuberances 19 are positioned on and proximal to distal end 18 of inner member 15. The protuberances are also positioned about the proximal end of collapsed stent 14 to engage and extend into cells 2 of the stent. These protuberances deploy the stent from the outer member passage by pushing the proximal end of the collapsed stent in operable direction 16, which in turn deploys the collapsed stent out of outer member passage 12 and into an expanded condition. Concomitantly, outer member 11 is withdrawn from the collapsed stent in operable direction 13. As a result, distal portion 44 of the self-expanding stent is deployed from the outer member passage to an expanded condition at designated position 42 in the body passage. As the inner member is pushed forward and outer member 11 is pulled back from the collapsed stent, remaining portion 45 of the stent is deployed from the outer member passage and into an expanded condition. Furthermore, it is to be kept in mind that the self-expanding stent once deployed from the outer member passage remains fixedly positioned longitudinally at designated position 42 in the body passage.

Figure 3:
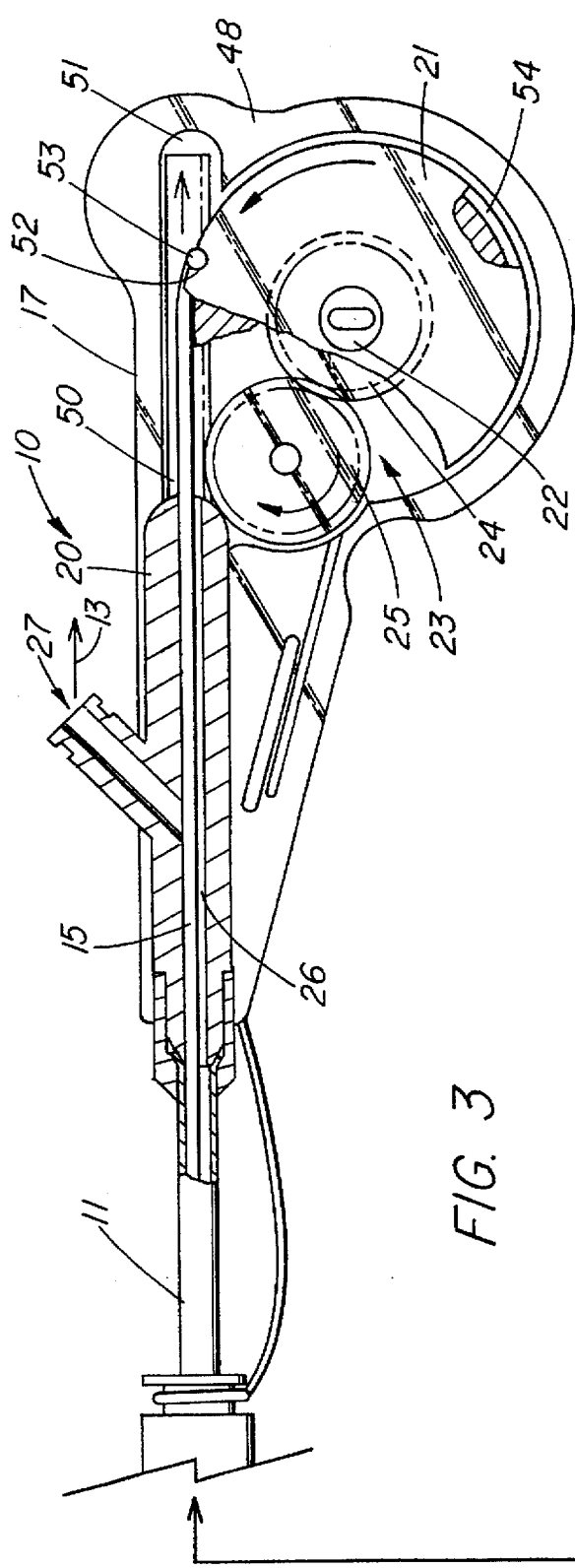
FIG. 3 depicts a partially sectioned view of the introducer of FIG. 1 with the self-expanding stent fully deployed in a body vessel.
Figure 3:
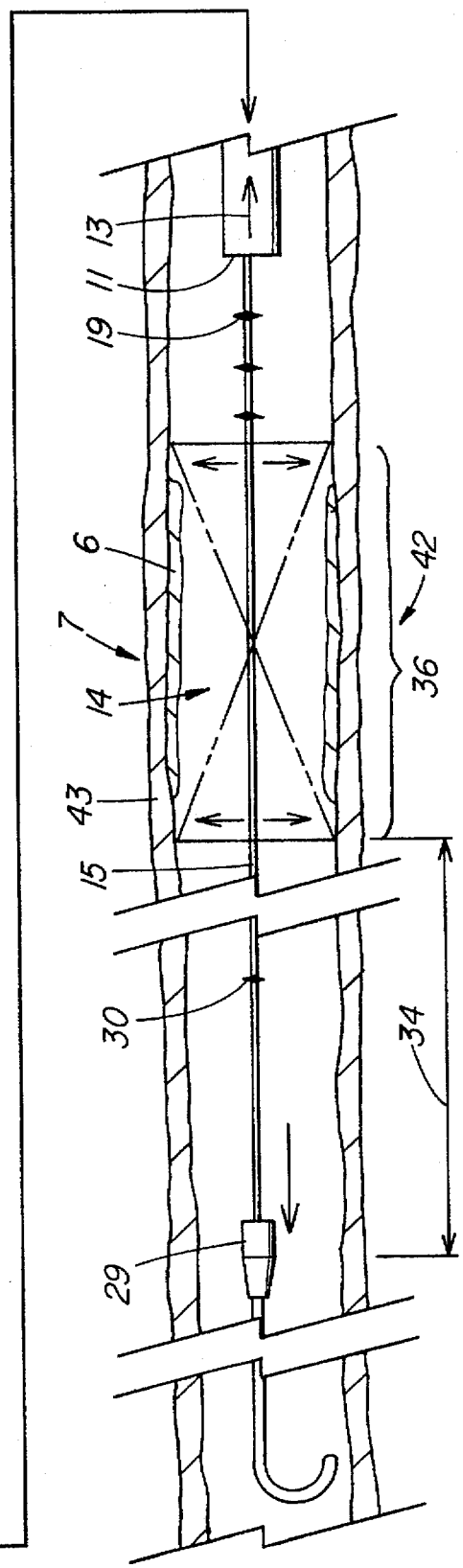

FIG. 3 depicts a partially sectioned view of introducer 10 of FIG. 1 with self-expanding stent 14 fully deployed at designated position 42 in body passage 43. As depicted, self-expanding stent 14 is in a fully expanded condition, thereby mechanically supporting plaque 6 or any intimal flap at occlusion site 7.

FIGS. 2 and 3 also depict a partially sectioned view of interconnection mechanism 17 including outer member carrier 20 connected to outer member tube 11 and inner member carrier 21 connected to inner wire guide member 15. Carrier 20 includes a carrier passage 26 extending longitudinally therethrough with inner member 15 extending through the carrier passage. The outer member carrier is slidably housed in handle casing 48 and moves longitudinally in operable direction 13. The outer member carrier also includes sideport 27 communicating with the carrier passage, which in turn communicates with outer member passage 12. The sideport allows for the introduction of fluids such as contrast media and medications should the need arise during the placement procedure. A toothed rack 50 is connected to outer member carrier 20 and longitudinally slides in rack channel 51 provided in handle casing 48. A second or inner member carrier 21 is dish shaped and is rotatably positioned in handle casing 48. The outer circular edge of the inner member carrier includes a recessed channel or groove 54 for cradling inner member 15. The inner member is connected to the inner member carrier 21 at the outer edge thereof in transverse channel 52 with the aid of a well-known cross pin 53.

Figure 4:
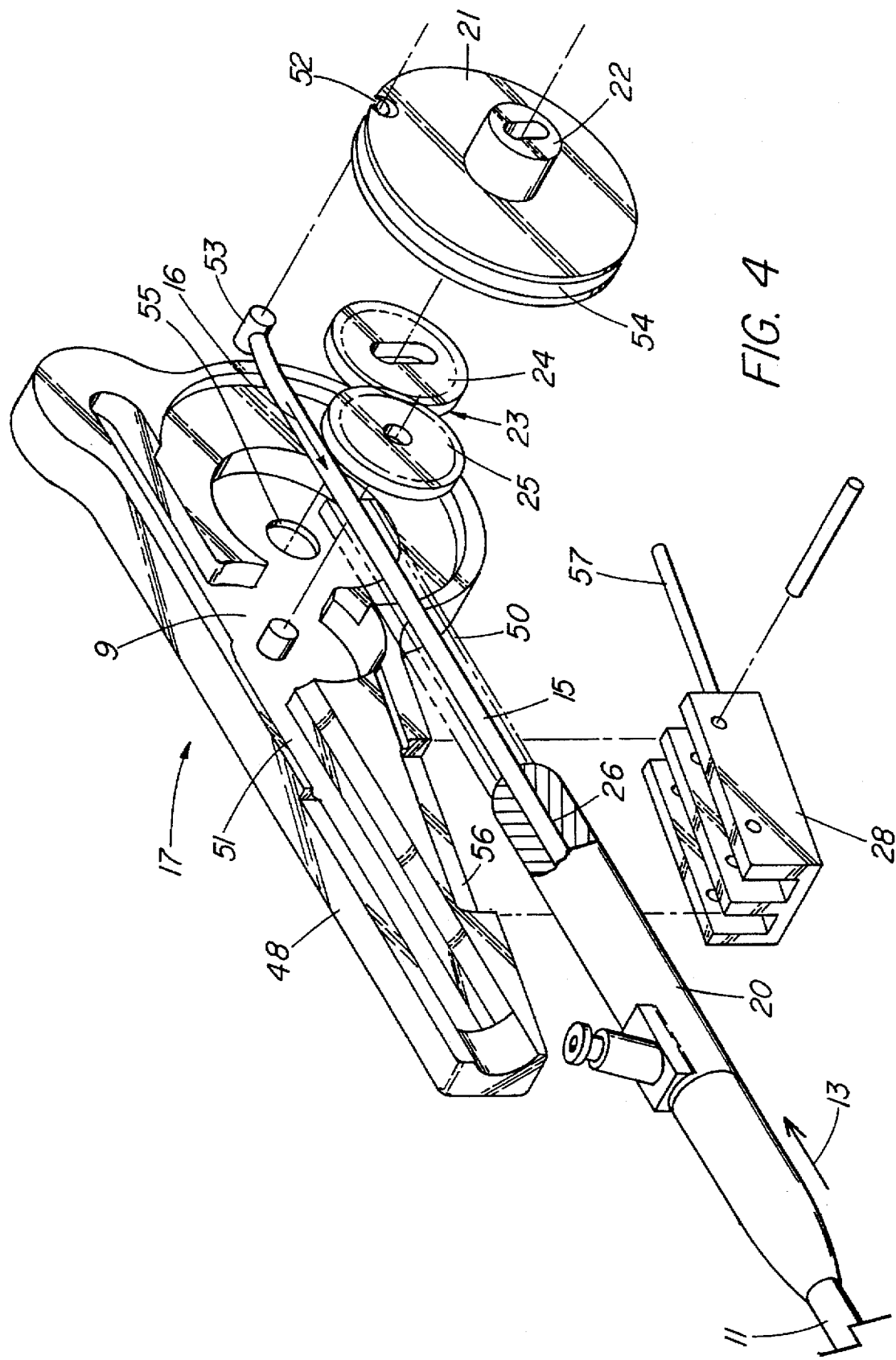
FIG. 4 is an enlarged, exploded view of the interconnection mechanism of FIGS. 1–3.

FIG. 4 is an enlarged, exploded view of interconnection mechanism 17 of FIGS. 1–3. One half of handle casing 48 is shown with rack channel 51 longitudinally positioned therein for receiving toothed rack 50 and output member carrier 20. Inner wire guide member 15 extends through carrier passage 26 of outer member carrier 20 and attaches to inner member, dish-shaped carrier 21 in transverse channel 52 with cross pin 53. Recessed channel 54 extends circumferentially around inner member carrier 21 for receiving and guiding inner wire guide member 15. Interconnection mechanism 17 also includes input drive member 22, which is coupled to inner member carrier 21. Input drive member 22 comprises a hub connected to inner member carrier 21 at its central axis and rotatably rides in handle casing hole 55 in each of the casing halves. A drive wheel 8 (depicted in FIG. 1) is connected to input drive member 22 on either side of the handle casing for either left- or right-hand operation of the introducer by the physician. Rotation of the drive wheel, as well as the input drive member, causes movement of outer member carrier 20 in operable direction 13 and movement of inner member carrier 21 in operable direction 16.

Interconnection mechanism 17 also includes a transfer assembly 23 coupled to input drive member 22 and at least one of the outer and inner member carriers 20 and 21. In this preferred embodiment, the transfer assembly is directly coupled to outer member carrier 20 via toothed rack 50 and indirectly coupled to input member carrier 21 via input drive member 22. The transfer assembly includes a drive member gear 24 connected to input drive member 22 and an intermediate member gear 25 coupled to the outer member carrier 20 via toothed rack 50. Intermediate gear 25 rotates in cylindrical recess 9 positioned in handle casing half 48. The transfer assembly further includes toothed rack 50, which longitudinally slides in rack channel 51. The size of each gear as well as the number of teeth therein is selected to operate the outer member 11 operational distance 33 in operable direction 13 and inner member 15 operational distance 34 in operable direction 16. In this preferred embodiment, operational direction 13 is opposite in direction to operational direction 16. Outer member operational distance 33 is approximately the short length 36 of stent 14 in a fully expanded condition, which was previously described as 40 mm in length. Inner member operational distance 34 was previously described as the difference in short length 36 and long length 35 of the stent in the expanded and the collapsed conditions, respectively. Thus, inner member operational distance 34 was previously calculated and described for a 10 mm diameter stent as approximately 115 mm.

Interconnection mechanism 17 also includes a lock 28 for limiting movement of the outer and inner members. Lock 28 includes a thumb slide insertable in handle casing recess 56 for sliding longitudinally therein and extending lock pin 57 into and out of the teeth of intermediate gear 25. Lock 28 limits movement of the inner and outer members until the introducer and collapsed stent have been properly positioned at the designated site in the body vessel or duct.

Prior to complete deployment of self-expanding stent 14, the direction of the input and output members can be reversed by the introducer to retract the stent into outer member passage 12. This feature is utilized by the physician should unexpected movement of the introducer and/or stent occur during the deployment procedure. Furthermore, the interconnection mechanism 17 has been described as including a transfer assembly for operating inner and outer members in opposite directions with different operational distances. As can be readily seen by one skilled in the art, the transfer assembly can be fashioned by using only one gear so as to operate both the inner and outer members in the same operable direction. The size of the drive member gear, as well as the rack teeth, can also be varied to change the length of inner and outer member operable distances. This is done to accommodate different diameter stents as well as the short (expanded) and long (collapsed) lengths thereof.

Figure 5:
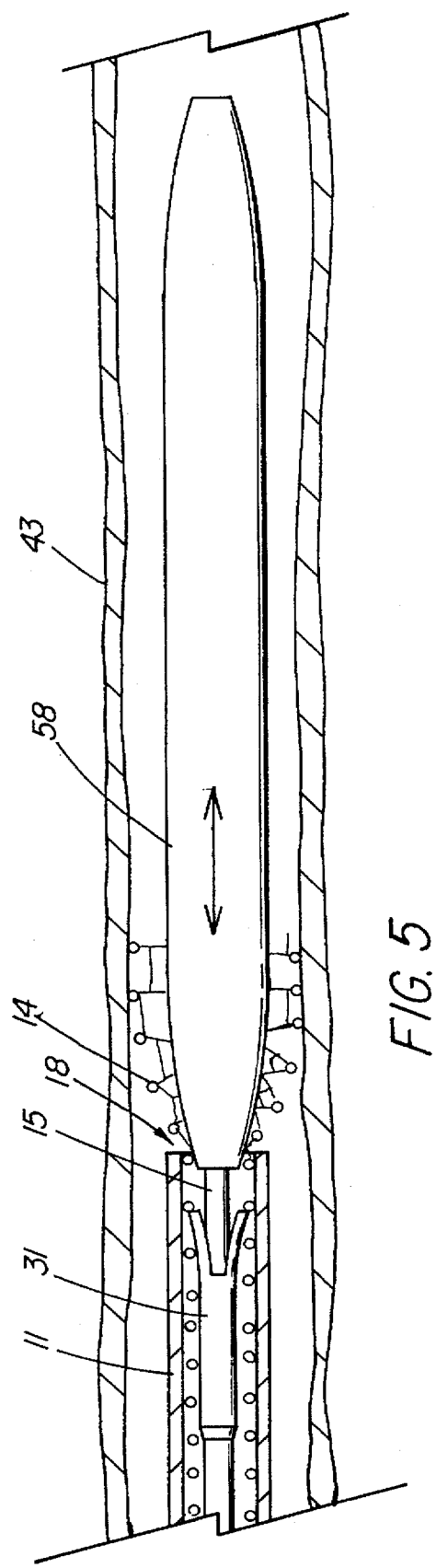
FIG. 5 depicts an alternative embodiment of the inner member of the stent introducer of FIGS. 1–4.

FIG. 5 depicts an alternative embodiment of inner member 15, in which a distal end protuberance 31 is positioned near the distal end of the inner member. The collapsed stent is positioned proximal of radially enlarged, distal inner member tip 58. Protuberance 31 comprises a forked cannula soldered to inner member 15. Protuberance 31 engages the distal end of the stent and pulls, rather than pushes, the collapsed stent from outer member passage 12. Protuberance 31 is used with a ratcheting motion in and out of outer member passage to pull the stent out of outer member passage 12 as outer member 11 is concomitantly withdrawn from the collapsed stent as previously described. As a result, the distal end of inner member 15 extends only minimally past the occlusion site. Thus, trauma to the body vessel or duct extending beyond the occlusion site is minimized. Of course, transfer assembly 23 is modified in a well-known manner to provide the ratcheting motion of inner member 15.

It is to be understood that the above-described stent introducers is merely an illustrative embodiment of the principles of this invention and that other stent introducers may be devised by those skilled in the art without departing from the spirit and scope of this invention. It is contemplated that the operable distances and directions of the inner and outer members can be readily varied as previously suggested. Furthermore, deployment of the self-expanding stent can be used with a ratcheting motion, a continual motion, or combinations thereof, which should be readily apparent to those skilled in the art for deploying a stent having various anatomical constraints placed thereon.

What is claimed is:

1. Stent introducer (10) comprising:
    an outer elongated member (11) having an outer member passage (12) extending longitudinally therein and a first operable direction (13) for deploying a self-expanding stent (14) from said outer member passage;
    an inner elongated member (15) positioned in said outer member passage and having a second operable direction (16) for deploying said stent from said outer member passage; and
    an interconnection mechanism (17) connected to said outer and said inner members and operable for simultaneously operating said outer member in said first direction for a pre-selected distance and said inner member in said second direction for a pre-selected distance, whereby said stent in a collapsed condition is deployed from said outer member passage to an expanded condition and wherein said stent is longitudinally fixed in position during expansion to said expanded condition.

2. The stent introducer of claim 1 wherein said inner member includes at least one protuberance (19) for pushing a stent out of said outer member passage.

3. The stent introducer of claim 1 wherein said interconnection mechanism includes a first carrier (20) connected to said outer member for operating said outer member in said first direction and a second carrier (21) connected to said inner member for operating said inner member in said second direction.

4. The stent introducer of claim 3 wherein said interconnection mechanism also includes an input member (22) coupled to said first and said second carriers, for operating said outer member in said first direction for a first distance (33) and said inner member in said second direction for a second distance (34).

5. The stent introducer of claim 4 wherein said interconnection mechanism further includes a transfer assembly (23) coupled to said input member and at least one of said first and said second carriers.

6. The stent introducer of claim 5 wherein said transfer assembly includes a drive member (24) coupled to said input member and an intermediate member (25) coupled to said first and second carriers.

7. The stent introducer of claim 3 wherein said first carrier includes a carrier passage (26) extending therethrough and communicating with said outer member passage, wherein said inner member extends through said carrier passage, and wherein said second direction of said inner member is opposite to said first direction of said outer member.

8. The stent introducer of claim 7 wherein said first carrier also includes a sideport (27) communicating with said outer member passage.

9. The stent introducer of claim 1 wherein said interconnection mechanism further includes a lock (28) coupleable to at least one of said first and said second carriers for limiting movement thereof.

10. The stent introducer of claim 1 wherein said inner member further includes first and second radiopaque markers (29, 30) positioned about a distal end (18) of said inner member for indicating placement of a stent in an expanded condition.

11. The stent introducer of claim 1 wherein said inner member includes at least one protuberance (31) for pulling a stent out of said outer member passage.

12. The stent introducer of claim 1 wherein said inner member includes an atraumatic distal end (32).

13. Stent introducer (10) comprising:
   an outer elongated member (11) having an outer member passage (12) extending longitudinally therein and a first operable distance (33) for deploying a self-expanding stent (14) from said outer passage;
   an inner elongated member (15) positioned in said outer passage and having a second operable distance (34) for deploying said stent from said outer member passage, said first and second operable distances being related to a long length (35) of said stent in a collapsed condition and a short length (36) of said stent in an expanded condition; and
   an interconnection mechanism (17) coupled to said outer member and operable for simultaneously operating said outer and said inner members said first and said second operable distances, respectively, whereby said stent in said collapsed condition is deployed from said outer member passage to said expanded condition and wherein said stent is longitudinally fixed in position during expansion to said expanded condition.

14. The stent introducer of claim 13 wherein said outer member is operated in a first operable direction (13) and wherein said inner member is operated in a second operable direction (16) opposite to said first operable direction.

15. The stent introducer of claim 13 wherein said first operable distance (33) is at least the short length (36) of a stent in an expanded condition and wherein said second operable distance (34) is approximately the difference (37) in the long and short lengths of the stent.

16. The stent introducer of claim 13 wherein said inner member includes at least one protuberance (19, 31) for deploying a stent out of said outer member passage.

17. The stent introducer of claim 13 wherein said first and said second operable distances are related to the long and short lengths (35, 36) of a stent so that a distal end (38) of a stent being deployed from said outer member passage remains fixedly positioned longitudinally relative to said interconnection mechanism.

18. The stent introducer of claim 17 further comprising an introducer sheath (39) having a passage (40) in which said outer and said inner members are positioned and a distal end (41) that is fixedly positionable with respect to said interconnection mechanism.

19. Stent introducer (10) comprising:
   an outer elongated member (11) having an outer member passage (12) extending longitudinally therein and a first operable distance (33), said outer member being operable in a first direction (13) over said first distance for deploying a self-expanding stent (14) in a collapsed condition from said outer member passage;
   an inner elongated member (15) positioned in and extendable from said outer member passage and having a second operable distance (34), said inner member being operable in a second direction (16) opposite to said first direction for deploying said stent in said collapsed condition in said outer member passage, and said inner elongated member being operable over said second distance simultaneously with operation of said outer elongated member over said first distance: said first operable distance being at least the short length (36) of said stent in an expanded condition, said second operable distance being approximately the difference (37) in the long and short lengths of said stent, said inner member including at least one protuberance (19) for engaging said stent in said collapsed condition and deploying said stent from said outer member passage, said inner member also including first and second radiopaque markers (29, 30) positioned about an atraumatic distal end (32) thereof for indicating the position of said stent in said expanded condition; and
   an interconnection mechanism (17) including a first carrier (20) connected to said outer member and a second carrier (21) connected to said inner member; an input member (22) coupled to said second carrier; a transfer assembly (23) coupled to said input member and said first carrier; said first carrier including a carrier passage (26) extending therethrough and communicating with said outer member passage, said inner member extending through said carrier passage; and
   a lock (20) coupleable to least one of said first and second carriers for limiting the movement thereof;
   whereby said stent in said collapsed condition is deployed from said outer member passage to said expanded condition and wherein said stent is longitudinally fixed in position during expansion to said expanded condition.

20. A method of percutaneously deploying a self-expanding stent (14) in a body vessel or duct (43) comprising the steps of:
   positioning a self-expanding stent (14) in a collapsed condition around an inner member (15) and in an outer member passage (12) of a stent introducer (10);
   percutaneously introducing said self-expanding stent positioned in said stent introducer to a designated position (42) in a body vessel or duct (43);
   deploying from said outer member passage and with said inner member a distal portion (44) of said self-expanding stent to an expanded condition at the designated position in the body vessel or duct; and
   deploying from said outer member passage and with said inner member a remaining portion (45) of said self-expanding stent, said distal portion of said self-expanding stent remaining fixedly positioned longitudinally as said remaining portion is deployed from said outer member passage, wherein the step of deploying said distal portion includes the steps of withdrawing said outer member from said stent and pushing said inner member out of said outer member passage.

* * * * *